United States Patent
Li et al.

(10) Patent No.: US 11,986,250 B2
(45) Date of Patent: May 21, 2024

(54) NON-INVASIVE SYSTEM AND METHOD FOR TRACKING BONES

(71) Applicant: ORTHOSOFT ULC, Montreal (CA)

(72) Inventors: Di Li, LaSalle (CA); Louis-Philippe Amiot, Montréal (CA); Pierre Couture, Montreal (CA)

(73) Assignee: ORTHOSOFT ULC, Montréal (CA)

( * ) Notice: Subject to any disclaimer, the term of this patent is extended or adjusted under 35 U.S.C. 154(b) by 0 days.

(21) Appl. No.: 17/819,380

(22) Filed: Aug. 12, 2022

(65) Prior Publication Data
US 2022/0378508 A1    Dec. 1, 2022

Related U.S. Application Data

(62) Division of application No. 15/946,857, filed on Apr. 6, 2018, now Pat. No. 11,446,090.
(Continued)

(51) Int. Cl.
*A61B 34/10* (2016.01)
*A61B 5/00* (2006.01)
(Continued)

(52) U.S. Cl.
CPC ............ *A61B 34/10* (2016.02); *A61B 5/1072* (2013.01); *A61B 5/1075* (2013.01);
(Continued)

(58) Field of Classification Search
CPC ... A61B 34/10; A61B 34/20; A61B 2034/105; A61B 2034/2051; A61B 2034/2055;
(Continued)

(56) References Cited

U.S. PATENT DOCUMENTS

| 1,941,468 A | 1/1934 | Gilbert |
| 3,895,525 A | 7/1975 | Eichelberger et al. |
| | (Continued) | |

FOREIGN PATENT DOCUMENTS

| DE | 4231101 | 3/1994 |
| DE | 10136737 | 2/2003 |
| | (Continued) | |

OTHER PUBLICATIONS

Chen et al.—A system for ultrasound-guided computer-assisted orthopaedic surgery; published in 2005; Computer Aided Surgery, 10:5-6, pp. 281-292 (Year: 2005).
(Continued)

*Primary Examiner* — Chao Sheng
(74) *Attorney, Agent, or Firm* — NORTON ROSE FULBRIGHT CANADA LLP (57) ABSTRACT

Systems and methods for determining position and orientation of a bone of an anatomical feature are described. These include the use of a wearable holder configured to be mounted about an outer-skin surface of the anatomical feature, such that the anatomical feature and the bone are positioned in fixed relation with respect to the wearable holder when the wearable holder is mounted about the anatomical feature. Reference marker arrays are fixedly mounted to the wearable holder, each being positioned on the wearable holder to identify a landmark of the bone within the wearable holder when the wearable holder is mounted to the anatomical feature. The position and orientation of the reference markers are trackable to determine position and orientation of the wearable holder in a reference coordinate system, thereby enabling position and orientation of the landmarks on the bone to be determined.

16 Claims, 4 Drawing Sheets

Related U.S. Application Data (60) Provisional application No. 62/482,720, filed on Apr. 7, 2017.

(51) Int. Cl.

| | | |
|---|---|---|
| *A61B 5/107* | (2006.01) | |
| *A61B 5/11* | (2006.01) | |
| *A61B 8/00* | (2006.01) | |
| *A61B 8/08* | (2006.01) | |
| *A61B 34/00* | (2016.01) | |
| *A61B 34/20* | (2016.01) | |
| *A61B 90/00* | (2016.01) | |

(52) U.S. Cl.
CPC .......... *A61B 5/1127* (2013.01); *A61B 5/6828* (2013.01); *A61B 8/0875* (2013.01); *A61B 8/4227* (2013.01); *A61B 8/4245* (2013.01); *A61B 34/20* (2016.02); *A61B 2034/105* (2016.02); *A61B 2034/2051* (2016.02); *A61B 2034/2055* (2016.02); *A61B 2034/2063* (2016.02); *A61B 2034/2068* (2016.02); *A61B 2034/256* (2016.02); *A61B 90/361* (2016.02); *A61B 2090/378* (2016.02); *A61B 90/39* (2016.02); *A61B 2090/3983* (2016.02); *A61B 2090/3991* (2016.02)

(58) Field of Classification Search
CPC .... A61B 2034/2063; A61B 2034/2068; A61B 5/1072; A61B 5/1075; A61B 5/1127; A61B 5/6828; A61B 8/0875; A61B 8/4227; A61B 8/4245; A61B 90/361; A61B 90/39; A61B 2090/378; A61B 2090/3983; A61B 2090/3991
See application file for complete search history.

(56) References Cited

U.S. PATENT DOCUMENTS

| | | | |
|---|---|---|---|
| 4,305,296 A | 12/1981 | Green et al. | |
| 5,197,476 A | 3/1993 | Nowacki et al. | |
| 5,249,581 A | 10/1993 | Horbal et al. | |
| 6,106,463 A | 8/2000 | Wilk | |
| 6,122,541 A | 9/2000 | Cosman et al. | |
| 6,159,152 A | 12/2000 | Sumanaweera et al. | |
| 6,190,320 B1 | 2/2001 | Lelong | |
| 6,213,958 B1 | 4/2001 | Winder | |
| 6,314,310 B1 | 11/2001 | Ben-Haim et al. | |
| 6,390,982 B1 | 6/2002 | Bova et al. | |
| 6,514,219 B1 | 2/2003 | Guimond et al. | |
| 6,529,758 B2 | 3/2003 | Shahidi | |
| 6,585,651 B2 | 7/2003 | Nolte et al. | |
| 6,585,731 B1 | 7/2003 | Rattner et al. | |
| 6,702,746 B1 | 3/2004 | Srouji | |
| 6,725,082 B2 | 4/2004 | Sati et al. | |
| 6,746,402 B2 | 6/2004 | Ustuner | |
| 6,768,496 B2 | 7/2004 | Bieger et al. | |
| 8,152,726 B2 | 4/2012 | Amiot et al. | |
| 2002/0065461 A1 | 5/2002 | Cosman | |
| 2002/0087101 A1 | 7/2002 | Barrick et al. | |
| 2002/0120192 A1 | 8/2002 | Nolte et al. | |
| 2003/0018255 A1 | 1/2003 | Martin et al. | |
| 2003/0036762 A1 | 2/2003 | Kerr et al. | |
| 2004/0068260 A1 | 4/2004 | Cossette et al. | |
| 2004/0147839 A1 | 7/2004 | Moctezuma | |
| 2004/0230199 A1 | 11/2004 | Jansen et al. | |
| 2005/0015022 A1 | 1/2005 | Richard et al. | |
| 2005/0085720 A1 | 4/2005 | Jascob et al. | |
| 2005/0085822 A1 | 4/2005 | Thornberry et al. | |
| 2005/0101866 A1 | 5/2005 | Goodwin | |
| 2005/0143676 A1 | 6/2005 | De Guise et al. | |
| 2005/0238216 A1 | 10/2005 | Yoden | |
| 2006/0262961 A1* | 11/2006 | Holsing | G06T 7/70 382/128 |
| 2007/0073121 A1 | 3/2007 | Hoarau et al. | |
| 2007/0100325 A1 | 3/2007 | Jutras et al. | |
| 2007/0225595 A1 | 9/2007 | Malackowski et al. | |
| 2008/0021309 A1 | 1/2008 | Amiot et al. | |
| 2008/0071195 A1* | 3/2008 | Cuellar | A61B 90/36 600/595 |
| 2009/0018445 A1* | 1/2009 | Schers | A61B 8/483 600/437 |
| 2012/0165707 A1 | 6/2012 | Amiot et al. | |
| 2013/0253379 A1 | 9/2013 | Mahfouz et al. | |
| 2014/0188132 A1* | 7/2014 | Kang | A61B 6/4441 606/130 |
| 2021/0307842 A1* | 10/2021 | May | A61B 5/064 |

FOREIGN PATENT DOCUMENTS

| | | |
|---|---|---|
| DE | 10346615 | 5/2005 |
| EP | 0353209 | 1/1990 |
| EP | 1161194 | 12/2001 |
| EP | 0966691 | 8/2005 |
| JP | 2005160704 | 6/2005 |
| WO | 2004/014488 | 3/2000 |
| WO | 2005/039391 | 7/2000 |
| WO | 2005/043319 | 7/2000 |
| WO | 0164094 | 9/2001 |
| WO | 0224075 | 3/2002 |
| WO | 0224094 | 3/2002 |
| WO | 03009772 | 2/2003 |
| WO | 2004/016178 | 2/2004 |
| WO | 2004/030559 | 4/2004 |
| WO | 2004/069073 | 8/2004 |
| WO | 2005/092198 | 10/2005 |
| WO | 2006/079211 | 8/2006 |
| WO | 2006092594 | 9/2006 |
| WO | 2006/128301 | 12/2006 |
| WO | 2009/059434 | 5/2009 |
| WO | 2009/111888 | 9/2009 |
| WO | 2010/088696 | 8/2010 |
| WO | 2015/022022 | 2/2015 |

OTHER PUBLICATIONS

"High-resolution 3D ultrasound jawbone surface imaging for diagnosis of periodontal bony defects: an in vitro study" Ann Biomed Eng. Nov. 2010;38(11):3409-22. doi: 10.1007/s10439-010-0089-0. Epub Jun. 8, 2010. https://www.ncbi.nlm.nih.gov/pubmed/20532630.

* cited by examiner

FIG. 4

NON-INVASIVE SYSTEM AND METHOD FOR TRACKING BONES

CROSS-REFERENCE TO RELATED APPLICATIONS

The present application is a divisional application of U.S. patent application Ser. No. 15/946,857 filed Apr. 6, 2018 which claims priority on U.S. Patent Application No. 62/482,720 filed Apr. 7, 2017, the entire contents of which are incorporated herein by reference.

TECHNICAL FIELD

The present disclosure relates to the field of computer-assisted medical procedures and, more specifically, to bone tracking and positioning in computer-assisted surgery (CAS) systems.

BACKGROUND

Computer-assisted surgery (CAS) makes use of markers fixed to the patient to track bones before and during surgery. Conventional trackable markers often include surgical pins which are inserted into the bones to be tracked. These pins, inserted into the bones before or during the surgery, may be of different diameter sizes and are relatively invasive. The insertion of such pins adds an extra step to the surgery and do not contribute to treatment, their only purpose being to assist surgical tracking of the bone. The installation of such pins can also be time-consuming.

Furthermore, the length of the pins is sometimes obtrusive to the surgeon who may therefore cut them to a length better adapted to her or his movement during the surgery. The need to sometimes cut the pins in this regard is also perceived as an additional step not particularly liked by surgeons, and the cut ends of pins may be sharp and hazardous to the personnel working around the surgery table.

An alternate option for tracking bones is to position optical trackers in relation to the bone to be tracked, for instance on soft tissue or on the pins themselves. However, in such a scenario, care must be taken to avoid movement of the optical trackers on the soft tissue, which may hamper the surgeon's maneuvers. Optical tracking is not always suitable because personnel or another object may block the optical signal, and therefore obstruct the line-of-sight between the sensor and the optical tracker.

SUMMARY

In accordance with one aspect of the present disclosure, there is provided a system for determining a position and an orientation of a bone of an anatomical feature, the bone underlying an outer-skin surface of the anatomical feature, the system comprising: a wearable holder configured to be mounted about the outer-skin surface of the anatomical feature, the anatomical feature and the bone being positioned in fixed relation with respect to the wearable holder when the wearable holder is mounted about the anatomical feature; at least two reference marker arrays fixedly mounted to the wearable holder, each said reference marker array being positioned on the wearable holder to identify a landmark of the bone underlying the wearable holder when the wearable holder is mounted about the anatomical feature, each said reference marker array including a plurality of reference markers; a fixed reference defining a reference coordinate system; a position sensing device operable to register position and orientation readings of the reference markers in the reference coordinate system; and a processing unit operable to receive the position and orientation readings and to measure time intervals, the processing unit being operable to determine the position and the orientation of the holder in the reference coordinate system for a given time interval.

In the system as defined above, the wearable holder may include a boot that is removably mountable about a foot and a lower leg.

In the system as defined above, the arrays may be positioned on the boot to overlie the landmarks of the foot and lower leg, the landmarks including medial and lateral malleoli of the ankle when the boot is mounted about the foot and the lower leg.

In the system as defined above, the reference marker arrays may be fixedly mounted to an immobile portion of the boot.

In the system as defined above, the reference markers may include active reference markers, each reference marker being operable to emit an electromagnetic wave, receive an echo of the wave off of a surface of the landmark, and record a time measurement for the echo.

In the system as defined above, the fixed reference may include a plurality of trackers fixedly mounted to a surgery table, each tracker being spaced apart from one another to define the reference coordinate system.

In the system as defined above, at least one of the reference markers may include an ultrasound device.

In the system as defined above, the fixed reference may include at least one ultrasound tracker.

In the system as defined above, the holder may include a belt being removably mountable about a leg.

In accordance with another aspect of the present disclosure, there is also provided a method for determining a position and an orientation of a bone of an anatomical feature, the bone underlying an outer-skin surface of the anatomical feature, the method comprising: removably attaching in a non-invasive manner a holder about an anatomical feature having the bone to fix a position of the anatomical feature and the bone with respect to the holder; identifying at least two landmarks of the bone, the landmarks being fixed in position with respect to the holder; registering position and orientation readings of reference markers fixedly mounted to the holder in a reference coordinate system; and determining the position and the orientation of the holder using the position and orientation readings of the reference markers to thereby determine the position and orientation of the landmarks of the bone in the reference coordinate system.

In the method as defined above, identifying the at least two landmarks may include identifying the at least two landmarks without imagery of the bone.

In the method as defined above, identifying the at least two landmarks may include measuring a distance between each reference marker and the corresponding landmark on the bone.

The method as defined above may further include tracking the landmarks of the bone by repeating said registering and said determining at different time intervals.

In the method as defined above, registering the position and orientation readings may include triangulating the position and orientation readings of the reference markers with at least two reference trackers fixed in position within the reference coordinate system.

In the method as defined above, identifying the at least two landmarks may include pre-operatively imaging the at least two landmarks.

In accordance with another aspect of the present disclosure, there is also provided a wearable holder that is trackable by a computer-assisted surgery system, the wearable holder comprising: a body removably mountable about an outer-skin surface of an anatomical feature having an bone, the anatomical feature and the bone being positioned in fixed relation with respect to the body when the body is mounted to the anatomical feature; and at least two reference marker arrays fixedly mounted to the body, each reference marker array being positioned on the body and operable to identify a landmark of the bone when the body is mounted about the anatomical feature, each of the reference marker arrays having a plurality of reference markers, a position and an orientation of the reference markers being trackable in a reference coordinate system to determine the position and the orientation of the body in the reference coordinate system.

In accordance with another aspect of the present disclosure, there is further provided a system for determining a position and an orientation of bone of an anatomical feature, the bone underlying an outer-skin surface of the anatomical feature, the system comprising: a wearable holder removably mountable about the outer-skin surface of the anatomical feature, the anatomical feature and the bone being positioned in fixed relation with respect to the holder when the wearable holder is mounted about the anatomical feature; at least one holder imaging device fixedly mounted to the wearable holder to obtain an image of a landmark of the bone at a given time interval; a bone imaging device operable to obtain a pre-operative image of the bone in its entirety, the position and the orientation of the bone in the pre-operative image being known in a reference coordinate system; and a processing unit operable to compare the image of the landmark at said time interval to the same landmark in the pre-operative image, the position and the orientation of any portion of the bone in the reference coordinate system at said time interval being determined by matching the image of the landmark to the same landmark in the pre-operative image.

In the system as defined above, the bone imaging device may be operable to construct the pre-operative image of the bone from at least two images taken in non-coplanar planes.

In the system as defined above, the image of the landmark may be obtainable by the at least one holder imaging device is a contour of the bone underlying the wearable holder.

The system as defined above may further include a plurality of reference markers fixedly mounted to the holder, the position and the orientation of the reference markers being trackable in the reference coordinate system to determine the position and the orientation of the holder in the reference coordinate system.

In the system as defined above, the wearable holder may include a first probe mountable about the outer-skin surface of an upper portion of the leg having an underlying femur, and a second probe mountable about the outer-skin surface of a lower portion of the leg having the underlying tibia.

In the system as defined above, the at least one holder imaging device may include an ultrasound imaging device.

In accordance with yet another aspect of the present disclosure, there is further provided a method for determining a position and an orientation of a bone of an anatomical feature, the method comprising: obtaining a pre-operative image of the bone in its entirety, the position and the orientation of the bone in the pre-operative image being known in a reference coordinate system; removably attaching in a non-invasive manner a holder to the anatomical feature to fix a position of the anatomical feature and the bone with respect to the holder; obtaining an image of a landmark of the bone at a given time interval with the holder, the landmark being fixed in position with respect to the holder; and determining the position and the orientation of any portion of the bone in the reference coordinate system at said time interval by matching the image of the landmark to the same landmark in the pre-operative image.

In the method as defined above, obtaining the pre-operative image may include constructing the pre-operative image from at least two images taken in non-coplanar planes.

In the method as defined above, obtaining an image of the landmark may include obtaining a contour of the bone underlying the holder.

The method as defined above may further include registering position and orientation readings of reference markers fixedly mounted to the holder in the reference coordinate system, and determining the position and the orientation of the holder using the position and orientation readings of the reference markers to thereby determine the position and orientation of the landmarks of the bone in the reference coordinate system.

BRIEF DESCRIPTION OF THE DRAWINGS

Reference is now made to the accompanying figures in which.

DETAILED DESCRIPTION

Figure 1:
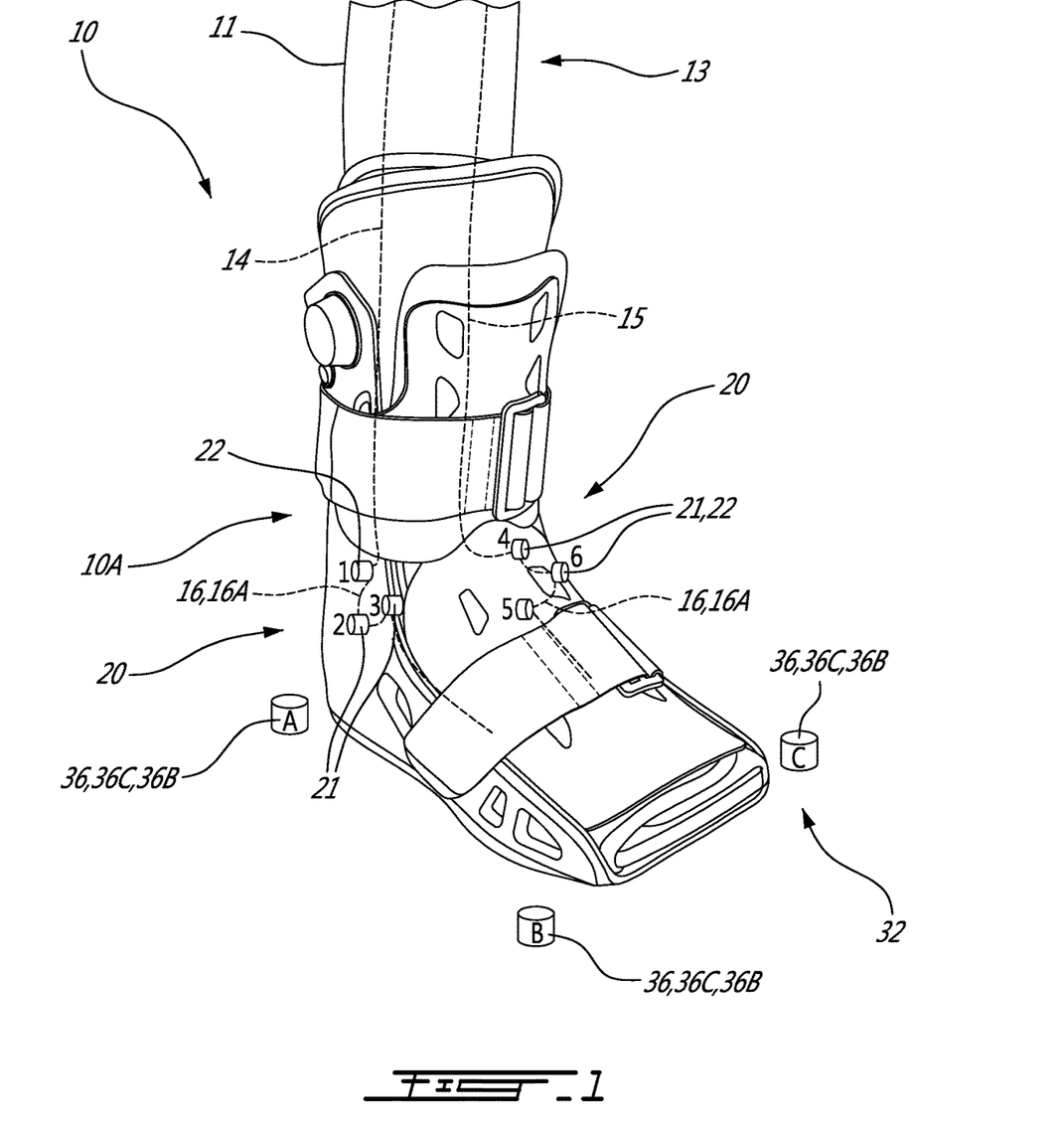
FIG. 1 is a perspective view of a holder being trackable in a computer-assisted surgery system, according to an embodiment of the present disclosure.

FIG. 1 illustrates a wearable holder 10 (or simply "holder" 10 as referred to herein) that is removably mounted about the outer-skin surface 11 (a.k.a., exposed skin, epidermis, external soft tissue, etc.) of an anatomical feature, such as but not limited to a lower leg portion 13 of a patient. The wearable holder 10 and the system using it, as will be described herein, may therefore be used to determine the position and/or orientation of body parts other than the lower leg portion 13 of a patient, such as anatomical features of arms (elbows, wrists, hands, etc.), other knee joints (e.g. knees, hips, etc.), and the like. The lower leg portion 13 includes a bone 14, which is a tibia 15 in the depicted embodiment. The bone is largely subcutaneous, in that a majority thereof is disposed beneath, and thus substantially underlies, the outer-skin surface 11 of the anatomical feature in question. In certain embodiments, the bone may thus be said to be substantially unexposed. However, it is to be understood that one or more portions of the bone 14 may be exposed during surgery, for example as a result of one or more incision(s) made as part of the surgical technique being employed. Accordingly, while portions of the bone 14 may be exposed during surgery with the anatomical feature within the holder 10, the bone will otherwise remain substantially subcutaneous. While the bone may be described herein as "underlying" the outer-skin surface, it is to be understood that this does not exclude the possibility that certain portions of the bone may at least partially exposed during surgery (e.g. by incisions, etc.) nor does this require or imply that the entirety of the bone must necessarily be unexposed and subcutaneous at all times.

The holder 10 is configured to be secured to the anatomical feature against which it is mounted in such a way that there is negligible or no movement between the holder 10 and the anatomical feature. The position and the orientation of the holder 10 are also trackable through space, whereby a tracking of the anatomical feature can be derived from a tracking of the holder 10. The holder 10 is therefore a non-invasive tool to be used to track the position and the orientation, and thus the movement, of the bone 14 through space. It is therefore appreciated that the holder 10 can take different forms to accomplish such functionality.

The holder 10 is in the form of a boot 10A in the depicted embodiment. In an alternate embodiment, the holder 10 is in the form a belt that is mounted to an anatomical feature (e.g. an arm and the underlying humerus bone, a leg and the underlying femur, etc.) of the patient to be in fixed relative relationship with the bone 14. In another alternate embodiment, the holder 10 is in the form a tight-fitting sleeve that is mounted to an anatomical feature of the patient to be in fixed relative relationship with the bone 14. Similarly, the holder 10 is mountable about other limbs, appendages, or other anatomical features of the patient having a bone 14 to be tracked.

When the holder 10 is mounted to the lower leg portion 13, the anatomical feature of the patient (the lower leg portion 13 in the illustrated embodiment) and the bone 14 (the tibia 15 in the illustrated embodiment) are in fixed relation with respect to the holder 10. The holder 10 is mounted about the lower leg portion 13 to substantially prevent the lower leg portion 13 and the foot from moving relative to the holder 10. This allows the position and the orientation of the lower leg portion 13 with respect to the holder 10 to remain substantially constant, and helps to track the movement of the bone 14 through space, as explained in greater detail below.

Two or more reference marker arrays 20 are fixedly mounted to the holder 10. Each reference marker array 20 is operable to identify a landmark 16 on the bone 14, and helps to track the position and the orientation of the landmark 16 through space. Each landmark 16 is a specific portion of the bone 14, in some instances a groove or a prominence on the bone 14, that serves as a guide to the location of other portions of the bone 14. Some non-limiting examples of bone landmarks 16 include the posterior and superior iliac crest in the pelvis, the medial and lateral malleoli in the ankle, the femoral neck, and the femoral epicondyles.

Each reference marker array 20 is in fixed relationship with the holder 10 such that the geometric relationship of each reference marker array 20 with the holder 10, and with the other reference marker arrays 20, is known. It will therefore be appreciated that since the position and the orientation of the bone 14 with respect to the holder 10 remains substantially constant, then the position and the orientation of the reference marker arrays 20 with respect to the bone 14 will also remain substantially constant.

In the depicted embodiment, each reference marker array 20 is spaced apart from the other reference marker array(s) 20. Each reference marker array 20 is mounted to a portion of the boot 10A which is stationary, and thus does not undergo displacement relative to the structure of the boot 10A. Therefore, the reference marker arrays 20 do not undergo displacement relative to one another, and thus their geometric relationship remains substantially constant even as the boot 10A undergoes movement.

In an alternate embodiment, one or more of the reference marker arrays 20 are mounted to a portion of the boot 10A which undergoes displacement. Therefore, the reference marker arrays 20 undergo displacement relative to one another in a known manner. Their geometric relationship therefore varies in a known fashion with the displacement of the boot 10A, and thus the relative movement between the reference marker arrays 20 can be compensated for.

Each reference marker array 20 has multiple reference markers 21. The term "reference marker" is intended to mean an active or passive marker, such as an emitter or a reflector. Each reference marker 21 is therefore an active or passive trackable object, and can operate using optical, RF, ultrasound, or electromagnetic signals. In FIG. 1, each reference marker 21 is fixedly mounted to the holder 10. Therefore, the reference markers 21 do not undergo displacement relative to the holder 10 and to one another, and thus their geometric relationship remains substantially constant even as the boot 10A undergoes movement. It will therefore be appreciated that since the position and the orientation of the bone 14 with respect to the holder 10 remains substantially constant, then the position and the orientation of the reference markers 21 with respect to the bone 14 will also remain substantially constant.

In the illustrated embodiment of FIG. 1, each reference marker array 20 includes three reference markers 21. The reference markers 21 are substantially flat and coplanar with the surface of the boot 10A. In an alternate embodiment, one or more of the reference markers 21 protrudes from the surface of the boot 10A away therefrom. The reference markers 21 of each array are located on a portion of the holder 10 which approximately overlies known bone landmarks 16. More particularly, in the depicted embodiment, the reference markers 21 are located on the boot 10A to overlie approximate locations of the medial and lateral malleoli 16A of the bones 14, i.e. the tibia and fibula. In embodiments where the holder 10 has a different form, the reference markers 21 are positioned to overlie the approximate locations of other bone landmarks 16.

Each reference marker array 20 is positioned on the holder 10 to identify a landmark 16 of the bone 14 and thus assist in the tracking of the bone 14 through space. In the embodiment of FIG. 1, two or more bone landmarks 16 are identified (i.e. the medial and lateral malleoli 16A). Typically, the greater the number of bone landmarks 16 that are identified, the more accurately the bone 14 can be tracked. Different techniques for non-invasively identifying the bone landmark 16 are within the scope of the present disclosure, and some are now discussed in greater detail.

In the embodiment of FIG. 1, the reference markers 21 of each reference marker array 20 are active. Stated differently, each reference marker 21 is operable to emit an electromagnetic wave, to receive an echo of the wave off of a surface of the bone landmark 16, and to record a time measurement for the echo. This helps to calculate a distance of the bone landmark 16 from each reference marker 21. In the illustrated embodiment where the holder 10 is in the form of a boot 10A and the reference markers 21 overlie approximate locations of the medial and lateral malleoli 16A of the bone 14, the value of the calculated distance will be indicative of the presence of the underlying medial and lateral malleoli 16A. In an embodiment, the distance to the tips of the medial and lateral malleoli 16A is calculable, such that an ankle axis passing through the tips of the medial and lateral malleoli 16A can be located. The value of the calculated distance can be matched to known values of the distance between the outer-skin surface 11 and the medial and lateral malleoli 16A for the specific patient. Therefore, when the value of the calculated distance (with appropriate compensation made for the thickness of the boot 10A) is substantially similar to the known values of the distance between the outer-skin surface 11 and the medial and lateral malleoli 16A, the calculated value will be indicative of the presence of medial and lateral malleoli 16A landmarks, and thus the reference arrays 20 will have identified the landmark 16. The presence of more than one reference marker 21 in each array 20 allows triangulation to ensure the accuracy of the position of the landmark 16. In the illustrated embodiment, one or more of the reference markers 21 includes an ultrasound device 22. The ultrasound device 22 is a transducer that emits an ultrasound wave and measures the time it takes for the wave to echo off of a hard surface (such as the bone landmark 16) and to return to the transducer face. Using the known speed of the ultrasound wave, the time measurement is translated into a distance measurement between the reference marker 21 and the bone landmark 16 located below the surface of the outer-skin surface 11. This distance measurement can then be compared to known distance measurements, as previously explained, to identify the bone landmark 16.

In an alternate embodiment where the reference markers 21 of each reference marker array 20 are also active, the reference markers 21 image the bone 14. Rather than using a measured or calculated distance to identify the bone landmark 16, one or more of the reference markers 21 in this embodiment operate the wave generation to produce sufficient echo to image the bone 14 in the vicinity of the reference marker 21. The localized image of the bone 14 is then compared to known images of the bones 14 to identify the bone landmark 16. In another alternate embodiment where the reference markers 21 of each reference marker array 20 are active, one or more of the reference markers 21 produce a contour of the bone 14 in the vicinity of the reference marker 21. The localized contour of the bone 14 is then compared to contours in known images of the bone 14 to identify the bone landmark 16. The known images may be acquired using any appropriate imaging technique including radiography, magnetic resonance, etc. The known images may then be processed to create digital three-dimensional models of the bone or bones 14, for the subsequent surface matching to be done to match the digital three-dimensional bone models to the data acquired by the reference markers 21 using ultrasounds or electromagnetic waves, for example. In the case of a digital three-dimensional model, a bone coordinate system may be virtually added to the model at pre-operative planning, for example axes, planes, etc.

In alternate embodiments, the reference markers 21 of each reference marker array 20 are passive and employ passive techniques to identify the bone landmarks 16. In one such embodiment where the holder 10 is in the form of a boot 10A, the passive reference markers 21 are positioned on the boot 10A in locations that are known to substantially overlie bone landmarks 16, such as the medial and lateral malleoli 16A. Each passive reference marker 21 includes a reflector. The distance between the reference markers 21 and the landmarks 16 can then be suitably approximated. As explained above, knowing this distance allows for the bone landmarks 16 to be tracked through space.

Figure 2:
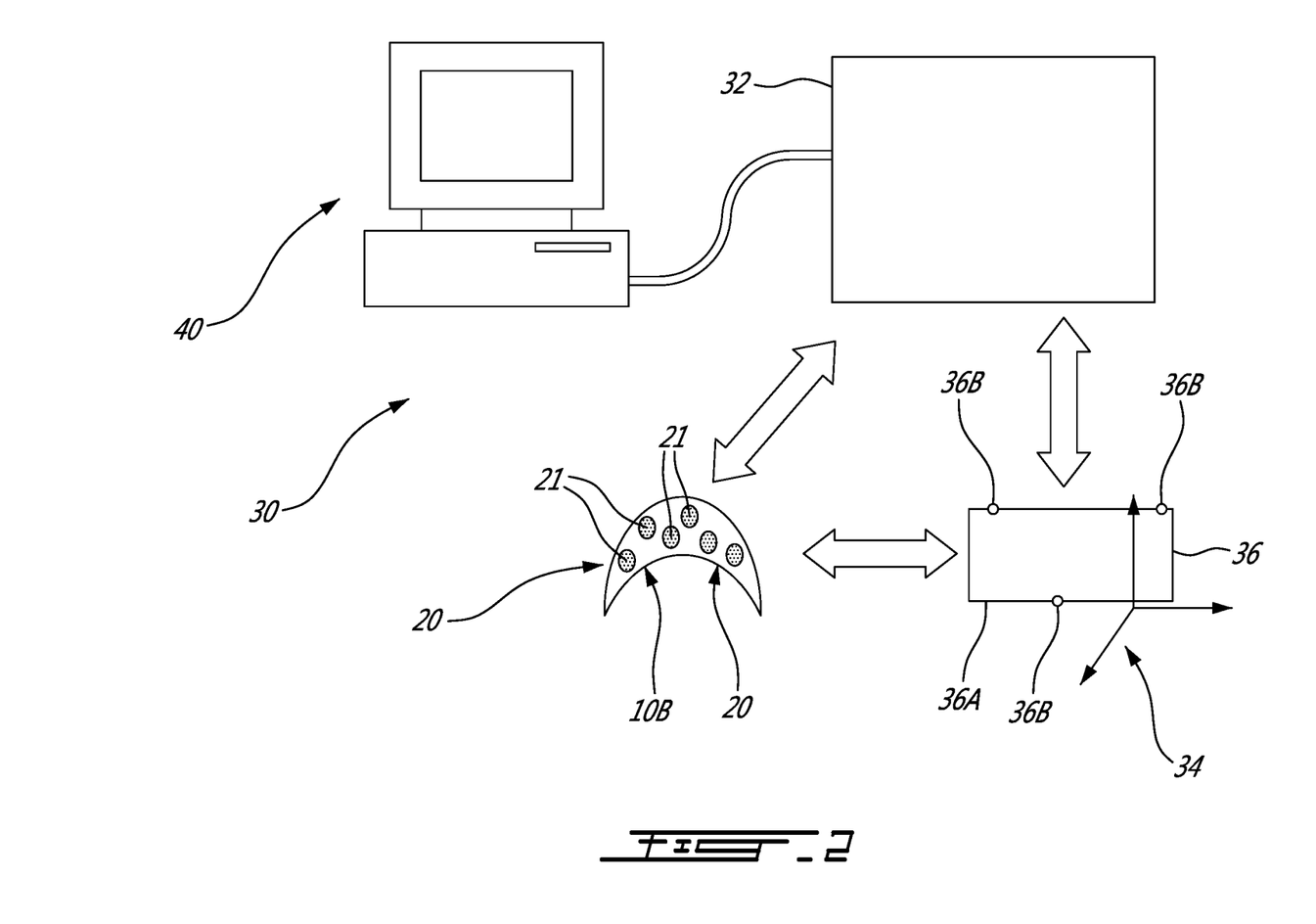
FIG. 2 is a diagram of a system for determining a position and an orientation of bone, which underlies an outer-skin surface, in space.

Referring to FIG. 2, there is also disclosed a system 30 for determining a position and an orientation of the bone 14 in space. The system 30 is a computer-assisted surgery (CAS) system. The system 30 includes one or more wearable holders 10. In the illustrated embodiment, the wearable holder 10 is in the form of a belt 10B, but it may also be for example the boot 10A. The belt 10B is removably mountable about the outer-skin surface 11 of an anatomical feature such as a leg having an underlying femur. The belt 10B is mounted about the leg to be positioned in fixed relation with respect to the underlying femur. The system 30 also includes the reference marker arrays 20 and the reference markers 21 which are similar to those described above and will therefore not be discussed in more detail. It will be noted that throughout the figures, like features are identified by like reference numerals.

The system 30 also includes a position sensing device 32. The position sensing device 32 is used with the CAS system 30 to continuously track the position and/or orientation in space of the reference markers 21, and thus, of the bone 14, as explained in greater detail below. The position and orientation of the reference markers 21 may be tracked in a reference coordinate system 34. According to an embodiment, the reference coordinate system 34 is defined by a fixed reference 36 that is separate from the moveable holder 10. Many different configurations of the position sensing device 32 which accomplish the above-described functionality are possible and within the scope of present disclosure. For example, and as shown in the illustrated embodiment, the position sensing device 32 is a distinct component which communicates with the reference markers 21 and with the fixed reference 36. In another embodiment, the position sensing device 32 is part of the fixed reference 36, as shown in FIG. 1 and described in greater detail below.

The fixed reference 36 has a known and a fixed position within the reference coordinate system 34 and is used to position and orient the holder 10, and thus the bone landmarks 16, in space within the reference coordinate system 34. The fixed reference 36 is therefore any active or passive device, with a known position in the reference coordinate system 34. In the illustrated embodiment of FIG. 2, the fixed reference 36 is the OR surgery table 36A which remains fixed in position within the reference coordinate system 34. A plurality of trackers 36B are fixedly mounted to the surgery table 36A. The trackers 36B are spaced apart from one another, and are calibrated before the surgery to define the reference coordinate system 34. According to an embodiment, the plane of the table, represented by the trackers 36B, is assumed to be and entered in the reference coordinate system 34 as being a frontal or sagittal plane of the patient lying in supine decubitus or lateral decubitus. The trackers 36B also communicate with the reference markers 21 on the holder 10 to track their position and orientation through space. It will therefore be appreciated that when the holder 10 is fixedly mounted about the anatomical feature, only the position and the orientation of the reference marker arrays 20 with respect to the fixed reference 36 will change as the bone 14 moves through space. The holder 10 thus functions to lock the bone 14 and the reference markers 21 as a rigid body allowing substantially no relative movement between these components.

In the embodiment of FIG. 1, the fixed reference 36 includes one or more ultrasound trackers 36C. The ultrasound trackers 36C are fixed in position and spaced apart from each other to define the reference coordinate system 34. The ultrasound trackers 36C form part of the position sensing device 32. They are operable to emit ultrasound waves and measure the time it takes for the wave to echo off of a corresponding reference marker 21 and to return to the ultrasound tracker 36C. Using the known speed of the ultrasound wave, the time measurement is translated into a distance measurement between the corresponding reference marker 21 and the ultrasound tracker 36C. This distance measurement can then be used to determine the position and orientation coordinates of the reference marker 21 within the reference coordinate system 34. Since the geometric relationship between the reference marker 21 and the landmark 16 is known, the distance measurement can also be used to determine the position and orientation coordinates of the bone landmark 16 within the reference coordinate system 34. In alternate embodiments, the trackers 36B of the fixed reference 36 emit other electromagnetic signals (e.g. RF), or emit optical signals.

In the illustrated embodiment of FIG. 1, the trackers 36B communicate with the reference markers 21 on the holder 10 to generate position and orientation readings by triangulation. At least two reference trackers 36B are fixed in position within the reference coordinate system 34. These at least two trackers 36B form two or more known points in the reference coordinate system 34, and a baseline length is determined between them. A third point in the reference coordinate system 34, such as the position of one of the reference markers 21, can then be determined with respect to the two points formed by the trackers 36B. Therefore, the position and/or orientation of the reference marker 21 can be determined within the reference coordinate system 34. The trackers 36B therefore track the location of the holder 10 in the reference coordinate system 34, and thus the location of the bone 14 fixed in position with respect to the holder 10, by triangulating the position of one or more reference markers 21 fixed on the holder 10 with respect to at least two reference trackers 36B in a known location in the reference coordinate system 34. Although the reference markers 21 are described as having the dual function of identifying landmarks, and being tracked, it is contemplated to provide other markers 21, such as passive markers, that will be tracked by the position sensing device 32.

Referring again to FIG. 2, the CAS system 30 also has a processing unit 40. The processing unit 40 is in communication with the position sensing device 32 to process the position and orientation readings of the reference markers 21. In some embodiments, the processing unit 40 is a part of the position sensing device 32. The processing unit 40 therefore includes any number of suitable components for performing the above functionality, such as an internal central processing unit (CPU), a memory unit, and a storage unit. The processing unit 40 can be any of a number of computing devices running a variety of applicable operating systems. The processing unit 40 may also include a display device, such as a monitor. The processing unit 40 may also include one or more input devices such as keyboards, pointing devices, and the like. The processing unit 40 runs various modules, in the form of algorithms, code, non-transient executable instructions, etc., in order to operate the CAS system 30 in the manner described herein.

Figure 3:
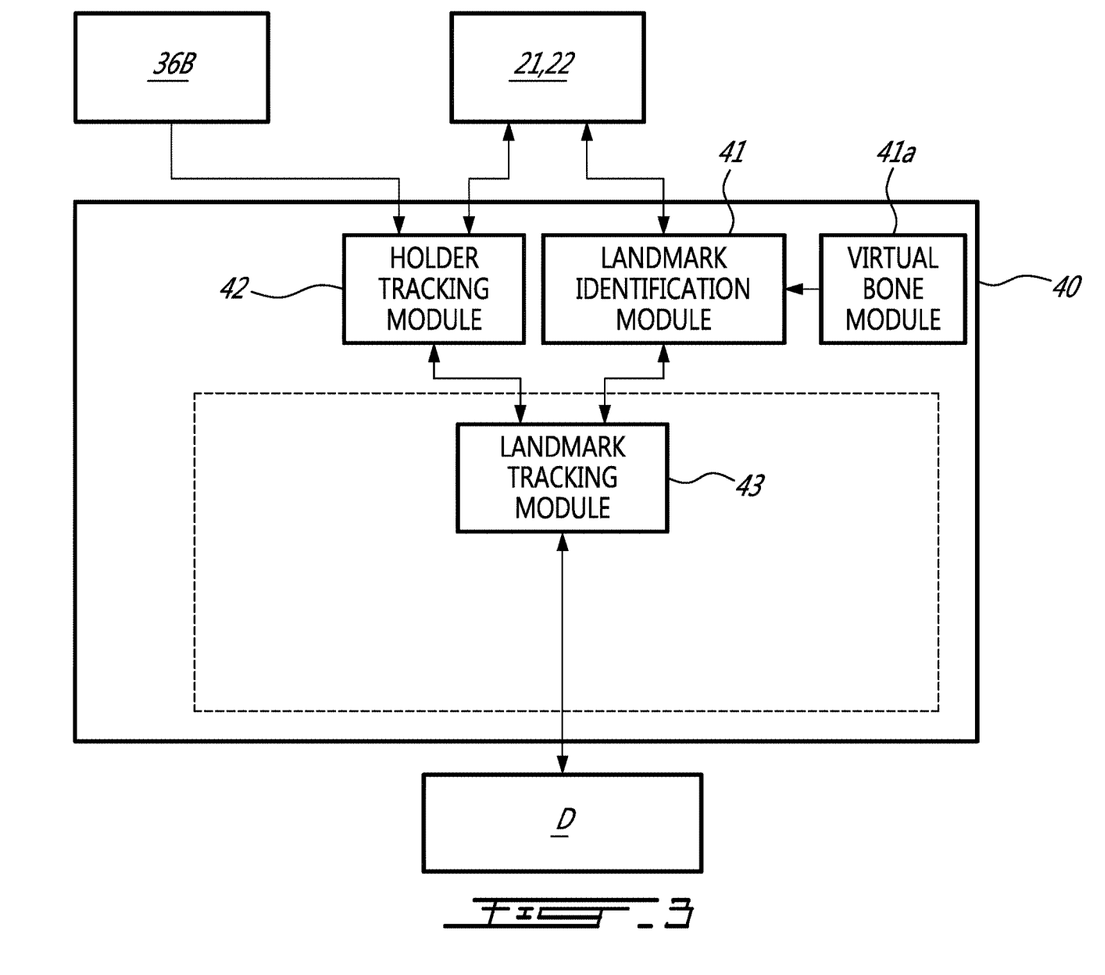
FIG. 3 is a block diagram of a processing unit of the system of FIG. 2.

Referring to the embodiment of the processing unit 40 shown in FIG. 3, the processing unit 40 includes, or communicates with, one or more interfaces D, for the information to be provided to the operator. The interfaces D may be monitors and/or screens including wireless portable devices (e.g., phones, tablets), audio guidance, LED displays, among many other possibilities. For example, the interface D comprises a graphic user interface (GUI) operated by the CAS system 30. The interface D may also display images outputted by the processing unit 40, for instance to track the bone 14 through space.

The processing unit 40 has a landmark identification module 41. The landmark identification module 41 is configured to output information indicative of the bone landmarks 16 to be tracked. In operation, the landmark identification module 41 receives data from the reference markers 21 of the reference arrays 20 and processes the data to identify the bone landmarks 16. The landmark identification module 41 is operable to process the data using any one of the different techniques for non-invasively identifying the bone landmark 16 described above. In an embodiment, the landmark identification module 41 commands the reference markers 21 or components thereof (e.g. ultrasound devices 22) to emit waves (electromagnetic, ultrasound) and then measures the time it takes for the wave to echo off of the bone landmark 16 and to return to the reference marker 21. Using the known speed of the wave, the landmark identification module 41 translates the time measurement into a distance measurement between the reference marker 21 and the bone landmark 16 located below the surface of the outer-skin surface 11. The landmark identification module 41 then compares this distance measurement to known distance measurements, for instance for confirmation, and outputs the identified bone landmark 16. The landmark identification module 41 may use triangulation knowing the geometrical arrangement of the reference markers 21 in the array 20.

The landmark identification module 41 has a virtual bone module 41A. The virtual bone module 41A provides the landmark identification module 41 with an image of the bone 14 and/or the bone landmark 16. The virtual bone module 41A in an embodiment therefore receives image data of the bone 14 and/or landmark 16 from the reference markers 21. In an alternate embodiment, the virtual bone module 41A includes a database of images of bones 14 any one of which can be provided to the landmark identification module 41 to identify a bone landmark 16.

The processing unit 40 also has a holder tracking module 42. The holder tracking module 42 is configured to output position and orientation readings of the reference markers 21 or like markers on the holder 10 in the reference coordinate system 34. The position and orientation readings help to determine the position and orientation of the bone landmark 16 in the reference coordinate system 34, and thus help to track the bone 14 in the space. The holder tracking module 42 receives active feedback from the trackers 36B or 36C to determine the position of the reference markers 21 within the reference coordinate system 34. The holder tracking module 42 is operable to process data using any one of the different techniques for tracking the reference markers 21 or like holder markers described above. For example, the holder tracking module 42 can triangulate the position and orientation readings of the reference markers 21 with the two or more reference trackers 36B fixed in position within the reference coordinate system 34. More particularly, the holder tracking module 42 calculates the baseline length between the trackers 36B in the reference coordinate system 34. The holder tracking module 42 then determines the position and orientation of a third point in the reference coordinate system 34 (i.e. one of the reference markers 21) using triangulation with respect to the two points formed by the trackers 36B.

The processing unit 40 also has landmark tracking module 43. The landmark tracking module 43 in operation receives the position and orientation readings of the reference markers 21 from the holder tracking module 42. The landmark tracking module 43 in operation also receives the landmark 16 identification information from the landmark identification module 41. In an alternate embodiment, the landmark tracking module 43 in operation receives an image of the bone 14 and/or the bone landmark 16 from the virtual bone module 41A. With this information, the landmark tracking module 43 is able to generate data on the position and orientation of the bone landmarks 16 in order to track the position and/or orientation of the bone 14 within the reference coordinate system 34. The position and orientation readings of the reference markers 21 allow the landmark tracking module 43 to determine the position and orientation of the holder 10 in the reference coordinate system 34 because the geometric relationship between the reference markers 21 and the holder 10 is known. Since the position and orientation of the holder 10 within the reference coordinate system 34 is known, the landmark tracking module 43 is operable to determine the position and/or orientation of the bone landmarks 16 in the reference coordinate system 34 because the geometric relationship between the bone landmarks 16 and the holder 10 is known. Therefore, the landmark tracking module 43 is operable to track the bone 14 and its landmarks 16 through space within the reference coordinate system 34. The landmark tracking module 43 outputs position and orientation readings of the bone 14 to the interface D.

It will therefore be appreciated that the CAS system 30 disclosed herein allows the position and/or orientation of a bone 14 to be tracked in a reference coordinate system 34 by simply tracking the movement of a holder 10 mounted securely and non-invasively about the outer-skin surface 11 of the anatomical feature containing the bone 14. The position and orientation of the holder 10 is therefore actively tracked in the CAS system 30, and from the position and orientation readings of the holder 10, the CAS system 30 indirectly determines the position and/or orientation of the bone 14 underlying the holder 10 and in fixed geometric relationship therewith. In at least some of the embodiments described above, the CAS system 30 determines the position and/or orientation of the bone 14 without having to continuously image the bone 14 itself, which can reduce system processing times. Indeed, the CAS system 30 allows for bone tracking without having to continuously identify the bone landmark 16. The CAS system 30 and holder 10 can be used to identify the bone landmarks 16 only once, and because of the fixed relationship between the bone landmarks 16 and the holder 10, the CAS system 30 can operate to track only the holder 10 in order to determine the position and orientation of the bone 14 in space. If desired, the operator can update the identification of the bone landmark 16.

The holder 10 also helps to overcome problems encountered with relative movement between outer-skin surface 11 and bone 14. The holder 10 is fixedly mounted to the outer-skin surface 11, and thus reduces relative movement between the outer-skin surface and the holder 10. This contrasts with some conventional techniques for non-invasively tracking bones which rely on garments, socks, and the like. These relatively loose-fitting coverings can move with the outer-skin surface and are therefore not in fixed relation with the bone or anatomical feature.

Figure 4:
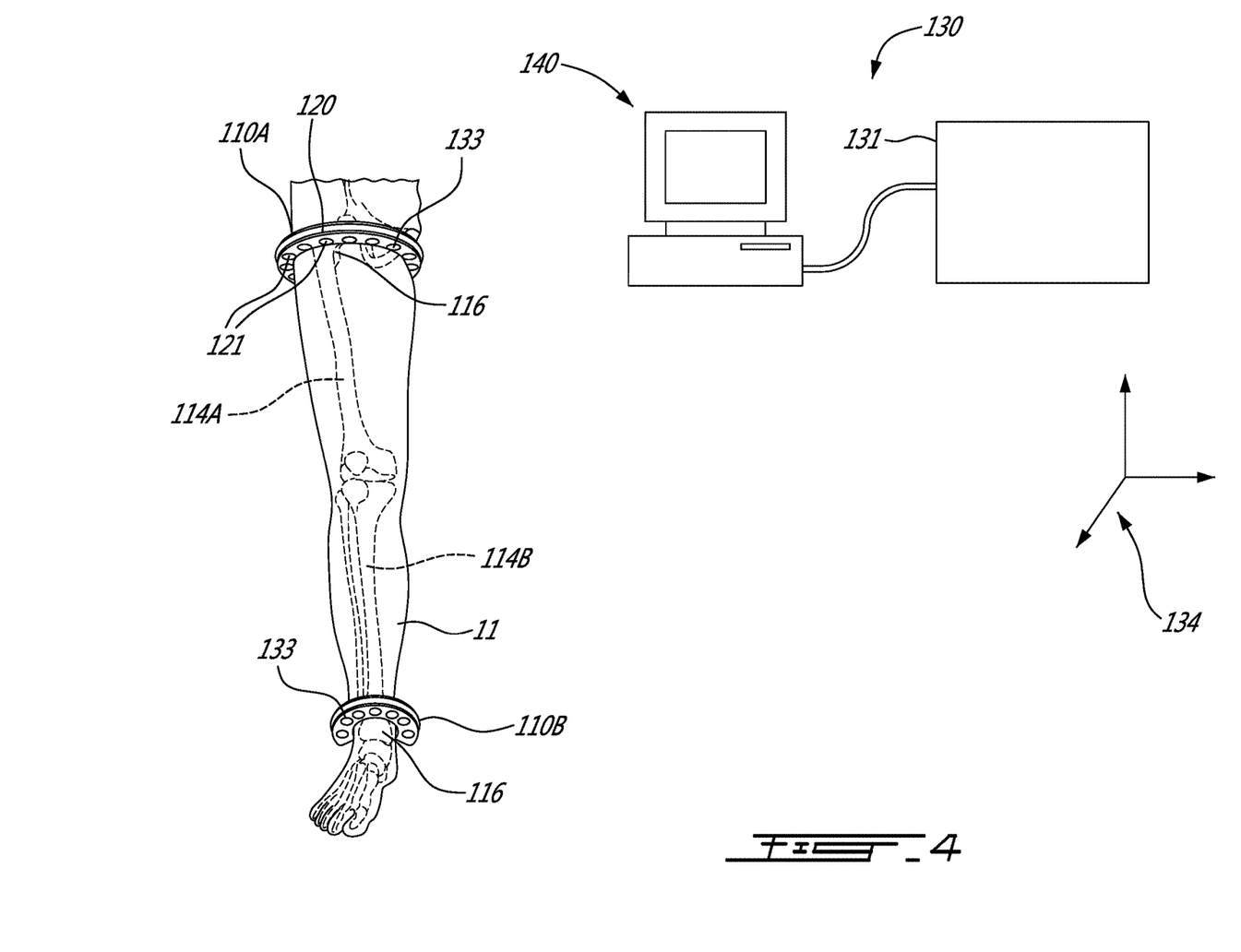
FIG. 4 is a diagram of another system for determining a position and an orientation of the bone in space.

FIG. 4 illustrates another embodiment of the system 130 for determining a position and an orientation of the bone 114 in the reference coordinate system 134. The system 130 also includes a wearable holder 110, reference marker arrays 120, and reference markers 121 which are similar to those described above and will therefore not be discussed in more detail. It will be noted that in FIG. 4 like features are identified by like reference numerals.

In the depicted embodiment, the CAS system 130 includes two wearable holders 110 or probes, each fixedly mounted about one of the bones 114 shown (i.e. the femur 114A and the tibia 114B). A first probe 110A in the form of a belt is mountable about the outer-skin surface 11 of an upper portion of the leg having the underlying femur 114A. A second probe 110B, also in the form of a belt, is mountable about the outer-skin surface 11 of a lower portion of the leg having the underlying tibia 114B. The probes 110A, 110B therefore allow tracking of the bones of the entire leg of the patient. More or fewer holders 110 can be used in the CAS system 130, and different bones 114 can be tracked in the CAS system 130.

In the depicted embodiment, each holder 110 has a plurality of reference markers 121 fixedly mounted to the holder 110. The position and the orientation of the reference markers 121 is trackable in the reference coordinate system 134, as explained above, so as to determine the position and the orientation of the holders 110 in the reference coordinate system 134. By tracking the holders 110 or probes, the position and orientation of the bone landmarks 116 may also be tracked.

The CAS system 130 includes a bone imaging device 131. The bone imaging device 131 operates to obtain a pre-operative image of the bone 114 in its entirety. The position and the orientation of the bone 114 when the pre-operative image is obtained is known in the reference coordinate system 134. The bone imaging device 131 can take many different configurations to accomplish the above-described functionality, some of which are now described in greater detail.

In a particular embodiment, the bone imaging device 131 is operable to construct the pre-operative image of the bone 114 from at least two images of the bone 114 taken in non-coplanar planes. For example, if the bone imaging device 131 includes an X-ray imager, it operates to generate views of the bone 114 in two orthogonal planes. The missing information of the bone 114 can then be constructed from the views in the orthogonal planes. Other CT (computed tomography) imaging techniques are also possible. Magnetic resonance imaging (MRI) can also be used.

In an alternate embodiment, the bone imaging device 131 includes a library of pre-operative bone images. A suitably corresponding pre-operative bone image can be retrieved from the library of images based on the particular characteristics of the patient (e.g. age, sex, race, height, weight, etc.). In yet another alternate embodiment, the bone imaging device 131 operates to obtain pre-operative images of the bone landmarks 116, and then constructs the bone 114 based on the imaged bone landmarks 116. Irrespective of the technique used to obtain the pre-operative image of the bone 114, the pre-operative image provides a "map" against which comparisons can be made. Stated differently, the pre-operative image of the bone 114 provides the position and orientation of the bone 114 and all its surfaces within the reference coordinate system 134. Comparing images taken during surgery to the pre-operative image helps to track the position and/or the orientation of the bone 114 in the reference coordinate system 134 during surgical procedures.

The CAS system 130 also includes one or more holder imaging devices 133. Each holder imaging device 133 is fixedly mounted to the holder 130 and operates to obtain an image of a landmark 116 of the bone 114 at different time intervals. The image of the landmark 116 can then be compared to the pre-operative image of the bone 114 to determine the position and/or orientation of the bone 114 within the reference coordinate system 134 at a given time interval.

In the depicted embodiment, the images produced by each holder imaging device 133 are in the form of a curve or contour of a portion the bone 114. The curve image is obtained by sweeping the bone 114 with the holder imaging devices 133. The holder imaging devices 133 therefore map in detail a portion of the bone 114. In an alternate embodiment, the image produced by each holder imaging device 133 is a three-dimensional image or reconstruction of the portion of the bone 114. It will be appreciated that the more accurate the image produced by each holder imaging device 133, the greater likelihood that it will be matched with the pre-operative image. In the depicted embodiment, each holder imaging device 133 is an ultrasound imaging device. In the depicted embodiment, each holder 110 has six holder imaging devices 133. More or fewer holder imaging devices 133 are within the scope of the present disclosure. The images of the landmark 116 and the pre-operative image of the bone 114 can be illustrated on an interactive or a non-interactive display device.

The processing unit 140 of the CAS system 130 is operable to receive the image of the landmark 116. The processing unit 140, or a module thereof, compares the image of the landmark 116 at a given time interval to the same landmark in the pre-operative image. The position and/or the orientation of any portion of the bone 114 in the reference coordinate system 134 at the time interval can therefore be determined by matching the image of the landmark 116 to the same landmark in the pre-operative image. Stated differently, the processing unit 140 operates to "register" features of the imaged bone 114 with the pre-operative image of the same bone 114. In recognizing the pattern of the bone landmarks 116 by matching the images, any movement (e.g. translation, rotation, etc.) of the bone 114 underlying the holder 110 with respect to the pre-operative image can be tracked in the reference coordinate system 134. Any shifts between the image of the landmark 116 and the landmark of the pre-operative image help to determine the position and/or orientation of any portion of the bone 114 relative to the pre-operative bone 114, and thus the position and/or orientation of any portion of the bone 114 in the reference coordinate system 134. The CAS system 130 therefore helps to build links with features of the bone 114 which the surgeon needs to track during surgical procedures, without having to actively track those features. Instead, the CAS system 130 can track landmarks 116 that are unimportant from a surgical perspective, and from this information, provide the position and orientation of features of the bone 114 that are of interest to the surgeon.

The above description is meant to be exemplary only, and one skilled in the art will recognize that changes may be made to the embodiments described without departing from the scope of the invention disclosed. Still other modifications which fall within the scope of the present invention will be apparent to those skilled in the art, in light of a review of this disclosure, and such modifications are intended to fall within the appended claims.

The invention claimed is:

1. A system for determining a position and an orientation of a bone of an anatomical feature, the bone underlying an outer-skin surface of the anatomical feature, the system comprising:
a wearable holder configured to be mounted about the outer-skin surface of the anatomical feature, the anatomical feature and the bone being positioned in fixed relation with respect to the wearable holder when the wearable holder is mounted about the anatomical feature;
at least two reference marker arrays fixed to the wearable holder, the at least two reference marker arrays including a first reference marker array and a second reference marker array spaced apart from the first reference marker array on the wearable holder, the first reference marker array being positioned on the wearable holder to identify a first bone landmark underlying the wearable holder when the wearable holder is mounted about the anatomical feature, and the second reference marker array being positioned on the wearable holder to identify a second bone landmark underlying the wearable holder, each of the first reference marker array and the second reference marker array including a plurality of reference markers;
a fixed reference defining a reference coordinate system;
a position sensing device configured to register position and orientation readings of the first reference marker array and the second reference marker array in the reference coordinate system; and
a processing unit configured to receive the position and orientation readings and to measure time intervals, the processing unit including a landmark identification module and a landmark tracking module that are configured to determine the position and the orientation of the first bone landmark and the second bone landmark in the reference coordinate system for a given time interval using the first reference marker array and the second reference marker array of the wearable holder.

2. The system as defined in claim 1, wherein the plurality of reference markers include active reference markers, each reference marker being configured to emit an electromagnetic wave, receive an echo of the wave off of a surface of the bone, and record a time measurement for the echo.

3. The system as defined in claim 1, wherein the fixed reference includes a plurality of trackers fixedly mounted to a surgery table, each tracker being spaced apart from one another to define the reference coordinate system.

4. The system as defined in claim 1, wherein at least one of the plurality of reference markers includes an ultrasound device.

5. The system as defined in claim 1, wherein the fixed reference includes at least one ultrasound tracker.

6. The system as defined in claim 1, wherein the wearable holder includes a belt configured to be removably mounted about a leg.

7. The system as defined in claim 1, wherein the wearable holder includes a boot being configured to be removably mounted about a foot and a lower leg.

8. The system as defined in claim 7, wherein the first bone landmark and the second bone landmark respectively include medial and lateral malleoli of the ankle when the boot is mounted about the foot and the lower leg.

9. The system as defined in claim 7, wherein the at least two reference marker arrays are fixedly mounted to an immobile portion of the boot.

10. A method for determining a position and an orientation of a bone of an anatomical feature, the bone underlying an outer-skin surface of the anatomical feature, the method comprising:
removably attaching in a non-invasive manner a holder about an anatomical feature having the bone to fix a position of the anatomical feature and the bone with respect to the holder;
identifying at least two landmarks of the bone using first and second reference marker arrays that are spaced apart and mounted on the holder, the landmarks being fixed in position with respect to the holder;
registering position and orientation readings of the first and second reference maker arrays in a reference coordinate system; and determining the position and the orientation of the holder using the position and orientation readings of the first and second reference marker arrays to thereby determine the position and orientation of respective ones of the at least two landmarks of the bone in the reference coordinate system.

11. The method as defined in claim 10, wherein identifying the at least two landmarks includes identifying the at least two landmarks without imagery of the bone.

12. The method as defined in claim 10, wherein identifying the at least two landmarks includes measuring a distance between each reference marker and the corresponding landmark on the bone.

13. The method as defined in claim 10, further comprising tracking the landmarks of the bone by repeating said registering and said determining at different time intervals.

14. The method as defined in claim 10, wherein registering the position and orientation readings includes triangulating the position and orientation readings of the reference markers with at least two reference trackers fixed in position within the reference coordinate system.

15. The method as defined in claim 10, wherein identifying the at least two landmarks includes pre-operatively imaging the at least two landmarks.

16. A wearable holder that is configured to be tracked by a computer-assisted surgery system, the wearable holder comprising:
a body configured to be removably mounted about an outer-skin surface of an anatomical feature having an bone, the anatomical feature and the bone being positioned in fixed relation with respect to the body when the body is mounted to the anatomical feature; and
at least two reference marker arrays fixedly mounted to the body and spaced apart from each other on the body, each of the at least two reference marker arrays being positioned on the body and configured to identify a respective landmark of the bone when the body is mounted about the anatomical feature, each of the at least two reference marker arrays having a plurality of reference markers, wherein a position and an orientation of the at least two reference marker arrays are configured to be tracked in a reference coordinate system to determine the position and the orientation of each of the respective landmark of the body in the reference coordinate system.

* * * * *